United States Patent [19]

Linder

[11] Patent Number: 5,251,617

[45] Date of Patent: Oct. 12, 1993

[54] ENDOTRACHEAL TUBE WITH CONCENTRICALLY MOUNTED AND AXIALLY SLIDABLE CONNECTOR

[76] Inventor: Gerald S. Linder, 16693 Charmel La., Pacific Palisades, Calif. 90272

[21] Appl. No.: 989,138

[22] Filed: Dec. 11, 1992

[51] Int. Cl.⁵ .......................................... A61M 16/00
[52] U.S. Cl. .......................... 128/200.26; 128/207.14; 128/207.15; 128/912; 128/DIG. 26
[58] Field of Search ................. 128/200.26, 207.14, 128/207.15, 207.16, 207.17, 207.29, 912, DIG. 26; 285/38, 175, 177, 235, 260

[56] References Cited

U.S. PATENT DOCUMENTS

| | | | |
|---|---|---|---|
| 4,152,017 | 5/1979 | Abramson | 285/260 |
| 4,369,991 | 1/1983 | Linder | 285/38 |
| 4,774,940 | 10/1988 | Linder | 128/912 |
| 4,877,025 | 10/1989 | Hanson | 128/912 |
| 4,909,248 | 3/1990 | Anderson | 128/207.14 |
| 5,184,611 | 2/1993 | Turnbull | 128/207.14 |

Primary Examiner—Edgar S. Burr
Assistant Examiner—Aaron J. Lewis
Attorney, Agent, or Firm—B. F. Spencer

[57] ABSTRACT

A flexible, cylindrical endotracheal tube is disclosed employing an axially slidable, hollow, cylindrical connector concentrically mounted upon the outer surface of the endotracheal tube near its proximal end. The proximal tip of the endotracheal tube is provided with an annular flange having an outer diameter larger than the inner diameter of the hollow output section of the slidable connector and smaller than the inner diameter of the hollow input section of the connector. A breathing circuit connector may be attached to the hollow input section of the slidable connector for coupling to the hoses of a conventional anesthesiology machine. The slidable connector is axially positionable over the outer surface of the proximal end portion of the endotracheal tube without loss of the airtight seal. The annular, flanged tip of the endotracheal tube may pass into and through the bore of the breathing circuit connector during positioning of the slidable connector. The axial positioning of the slidable connector may occur before intubation, after intubation, or while the patient is in recovery.

5 Claims, 1 Drawing Sheet

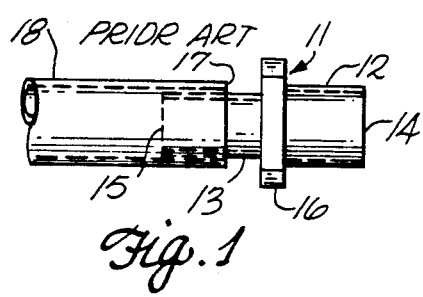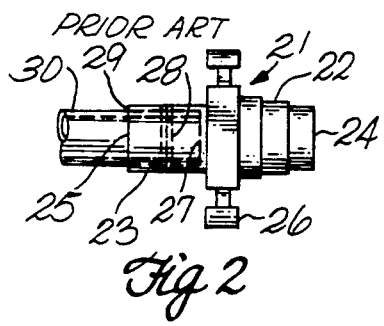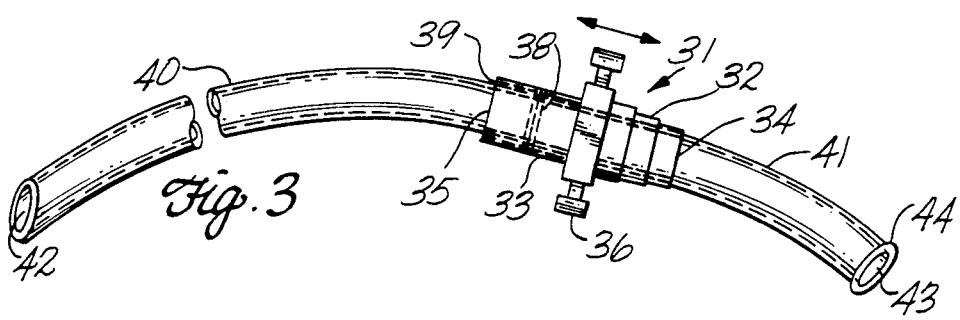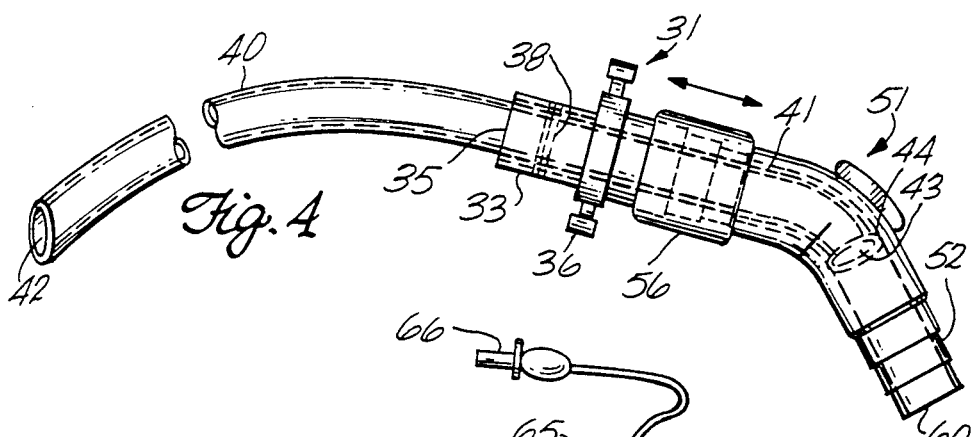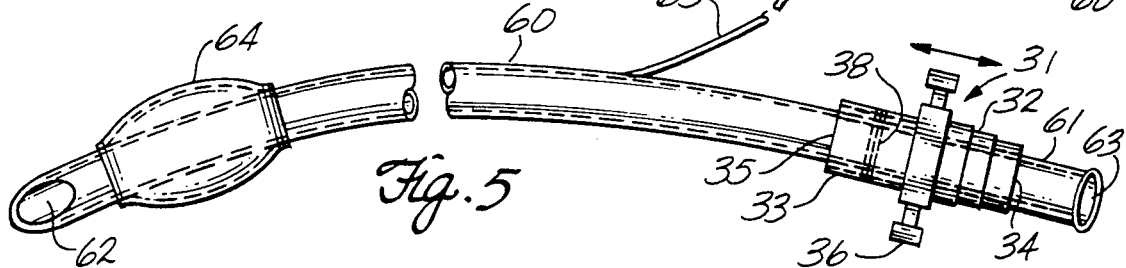

ENDOTRACHEAL TUBE WITH CONCENTRICALLY MOUNTED AND AXIALLY SLIDABLE CONNECTOR

BACKGROUND OF THE INVENTION

The present invention relates to medical catheters and endotracheal tubes.

The conventional medical catheter consists of a cylindrical, flexible tube having open proximal and distal ends and a central bore, or lumen, therethrough. The conventional endotracheal tube is of two types, one being a cuffed tube and the other being of the uncuffed type, with both types being considered as catheters. They vary in length and size, depending in part upon the age and physical size of the patient in which they are to be used.

Conventional endotracheal tubes are used with connectors to facilitate the coupling of the open proximal end of the tube to the hoses of the anesthesiology machine. There are two principal types of endotracheal tube connectors, both being formed of relatively hard plastic and consisting of a hollow, cylindrical output section, a hollow, cylindrical input section, and a central bore therethrough. In one type, the hollow cylindrical output section is a spout which is manually forced into the open proximal end of the cylindrical, flexible endotracheal tube to form a forced airtight seal. In the other type, the hollow cylindrical output section is provided with an inner annular ring or ridge projecting radially inward from the inside cylindrical wall. The annular ridge bears upon and slightly depresses the outer cylindrical surface of the proximal end portion of the endotracheal tube when this hollow cylindrical output section is concentrically forced upon the open proximal end of the tube. Both types provide an airtight seal between tube and connector. The hollow output sections of both types must be correctly dimensioned to mate with the many different sized and diameters of the tubes with which they are to be used. The hollow cylindrical input sections of these two types of connectors are of standard size; namely, fifteen millimeters. U.S. Pat. No. 4,369,991 shows and describes this second type of endotracheal tube connector.

The conventional breathing circuit connector consists of a hollow, cylindrical output section, a hollow, cylindrical input section, and a central bore therethrough. The cylindrical output section is of standard size; namely, fifteen millimeters, and is adapted for mated coupling to the fifteen-millimeter input section of the endotracheal tube connector. The Y-type breathing circuit connector has a hollow, cylindrical output section of standard size and a pair of hollow, cylindrical input sections, each input section coupled to a pair of flexible hoses, the proximal ends of which are connected to the conventional anesthesiology machine. U.S. Pat. No. 4,774,940 shows and describes representative examples of prior art breathing circuit connectors.

Due to the differences in the sizes and lengths of conventional catheters and endotracheal tubes, the practicing physician frequently finds it desirable to shorten the length of the proximal end portion of these tubes in order to place the open proximal end of the catheter or endotracheal tube, along with its attached connector, closer to the place where intubation is to occur. To achieve this shortening, the physician will remove a portion of the proximal end by cutting with a sharp knife. This shortening of the tube is frequently done by the anesthesiologist to permit the endotracheal tube, with its connector, breathing circuit connector, and their attached hoses, to be positioned closer to the face of the patient. This positioning, enables these connectors to be more easily attached to the patient's body or face, as by adhesive strips or tapes, to assure that the intubated endotracheal tube is securely and safely anchored against inadvertent movement. This shortening of the endotracheal tube is of some importance where larger and longer tubes are required, as in adults or large patients.

Where the endotracheal tube or catheter is supplied by the manufacturer with the connector already attached, it is necessary for the anesthesiologist to remove the connector from the proximal tip of the tube, cut off the desired length of the proximal end portion and reattach the connector. This reduction in the length of the endotracheal tube consumes time, exposes the endotracheal tube and removed connector to possible loss of sterility, and even the possibility of the removed connector being dropped or mislaid. Since the cutting is done prior to intubation, a loss of time is of some concern to the anesthesiologist, especially in emergency cases.

A solution to this problem is provided by this invention where the flexible, cylindrical endotracheal tube or catheter is provided with a hollow, cylindrical connector concentrically mounted upon the proximal end portion of the tube. The connector is designed to be axially slidable over the cylindrical surface of the proximal end portion to a position satisfactory to the using anesthesiologist. The proximal tip of the tube or catheter is provided with an annular ring or flange having a smooth, rounded periphery to permit the annular, flanged tip to readily enter into the bore or lumen of an attached breathing circuit connector, thus eliminating the necessity of having to cut or shorten the endotracheal tube.

Accordingly, it is an object of this invention to provide an endotracheal tube with a connector concentrically mounted upon the proximal end portion of the tube, the connector being axially slidable over the proximal end portion without loss of the airtight seal between connector and endotracheal tube.

It is another object of the invention to provide an endotracheal tube with a connector which may be axially slidable over the proximal end portion of the tube to position, or to reposition, the connector relative to the face of the patient without the necessity of removing the connector from the endotracheal tube.

BRIEF DESCRIPTION OF THE DRAWINGS

FIG. 1 illustrates one widely used type of connector shown attached to the proximal end of a catheter or endotracheal tube.

FIG. 2 is another prior art connector shown attached to the proximal end of a catheter or endotracheal tube.

FIG. 3 illustrates the present invention with a hollow, cylindrical connector concentrically mounted upon and slidably positionable over the outer cylindrical surface of a catheter near its proximal end.

FIG. 4 illustrates the invention of FIG. 3 with the hollow cylindrical input section of the slidable connector attached to a conventional breathing, circuit connector, and with the annular, flanged proximal tip of the catheter positioned within the breathing circuit connector.

FIG. 5 shows the invention employing a cuff-type endotracheal tube with concentrically mounted, slidable connector located on the proximal end portion near the annular, flanged proximal tip.

DESCRIPTION OF THE INVENTION

FIG. 1 illustrates a widely used prior art endotracheal tube connector 11 composed of hard plastic and consisting of a hollow, externally tapered cylindrical input section 12, a hollow, externally tapered cylindrical output section 13, and central bores 14 and 15 extending therebetween. A centrally located external flange portion 16, between the input and output sections 12 and 13, facilitates the holding of connector 11. The tapered output section 13, or spout, is shown forced into the open proximal end 17 of a conventional endotracheal tube or catheter 18.

FIG. 2 illustrates another prior art endotracheal tube connector 21 composed of hard plastic and consisting of a hollow cylindrical input section 22, a hollow cylindrical output section 23, and central bores 24 and 25 extending therebetween. A centrally located external flange 26 is provided for gripping connector 21. The hollow cylindrical input section 22, shown stepped, is of standard size for mated coupling to the cylindrical output section of the conventional fifteen-millimeter breathing circuit connector.

The hollow, cylindrical output section 23 is provided with an internal annular ring or ridge 28 of triangular cross section projecting radially inward from the hollow inside wall of section 23. Annular ridge 28 is laterally positioned approximately halfway between the open output end 29 of section 23 and the center of external flange 26. Annular ridge 28 extends into the central bore 25 by an amount approximately equal to the wall thickness of the endotracheal tube or catheter for which connector 21 is designed to be used. The tip of triangular-shaped ridge 28 is slightly rounded to prevent the tip from cutting into the outer cylindrical surface of the endotracheal tube or catheter.

Connector 21 is installed upon the open proximal end 27 of the catheter or endotracheal tube 30 by applying an axial force upon the connector until annular ridge 28 slides over the outer cylindrical surface of the catheter or endotracheal tube. The proximal end 27 of the catheter or endotracheal tube 30 abuts a stop within bore 25, as shown in FIG. 2. Connector 21 of FIG. 2 is shown and described in my aforesaid U.S. Pat. No. 4,369,991.

FIG. 3 illustrates the preferred embodiment of the invention wherein connector 31, similar in part to connector 21 of FIG. 2, is concentrically mounted upon the proximal end portion 41 of catheter or uncuffed endotracheal tube 40. Connector 31, composed of relatively hard plastic, includes hollow input section 32, hollow output section 33, central bores 34, 35, external flange 36, and an internal annular ring or ridge 38. The internal annular ring or ridge 38, of triangular-shaped cross section with rounded tip, depresses the outer cylindrical surface of catheter 40 to achieve an airtight seal between connector 31 and catheter 40.

There is no stop within bore 35 of connector 31, or within central flange 36, as is the case for connector 21 of FIG. 2. Accordingly, the central portion of catheter 40 extends completely through bores 33 and 35 of connector 31.

Connector 31 is axially slidable, as indicated by the arrows, over the outer cylindrical surface of catheter 40, either toward or away from the open, distal tip 42 of catheter 40. The hollow, cylindrical output section 33, with its bore 35, is dimensioned to slidably pass the appropriate size of catheter or endotracheal tube for which connector 31 is designed.

The diameter of bore 34 of hollow, cylindrical input section 32 is larger than the diameter of bore 35 of hollow, cylindrical output section 33, and is somewhat less than fifteen millimeters, the standard size of the input section of endotracheal tube connectors.

The proximal tip 43 of catheter 40 is provided with an annular ring or flange 44 having a smooth, rounded peripheral surface. The outer diameter of annular ring or flange 44 is dimensioned to be larger than the diameter of bore 35 of hollow output section 33 and less than the diameter of bore 34 of hollow input section 32 of connector 31, as will be explained hereinbelow.

FIG. 4 illustrates the preferred embodiment of the invention of FIG. 3 used together with one type of breathing circuit connector 51. Breathing circuit connector 51 is composed of relatively hard plastic and consists of a stepped hollow, cylindrical input section 52, an internally stepped hollow, cylindrical output section 56, and a central bore 60 extending therebetween. Breathing circuit connector 51 is identical to the breathing circuit connector shown in FIG. 4 of my aforementioned U.S. Pat. No. 4,774,940.

The diameter of bore 60 of breathing circuit connector 51 is substantially equal to the diameter of bore 34 of connector 31. Since the outer diameter of annular flange 44 is less than the diameter of bore 34 of connector 31, the outer diameter of annular flange 44 is, therefore, less than the diameter of bore 60 of breathing circuit connector 51. Accordingly, the proximal end portion 43 of catheter 40, with its annular flange 44, readily passes into and partly through bore 60 of breathing circuit connector 51, as shown in broken lines in FIG. 4. It is apparent, therefore, that both connectors 31 and 51 are axially positionable over the outer cylindrical surface of the proximal end portion 41 of catheter 40.

In view of the relative hardness of the material of which connector 51 is composed and the relative flexibility of the proximal end portion 41 of catheter 40, including its annular flange 44, the sliding of the annular flange 44, with its smooth, rounded periphery, within bore 60 is substantially friction-free. The small amount of bending of proximal end portion 41 of catheter 40 within bore 60 minimizes any likelihood of occluding the lumen of catheter 40.

The annular flange 44 may be integrally formed at the proximal tip 43 of catheter 40 as by heat expanding in a mold, or by separate attachment to the proximal tip 43 by chemical bonding.

Other types of breathing circuit connectors may be used with the present invention, including ones that are straight, or ones that are partly flexible, or the standard Y-type breathing circuit connector, as well as the 90-degree elbow connector. In the latter type, care must be exercised to limit the amount by which the connectors 31 and 51 may be slidably positioned over catheter 40 to prevent occlusion or blockage of the open annular, flanged tip 43 of catheter 40.

Since the diameter of annular flange 44 is less than the diameter of bore 34 of connector 31, the flanged, proximal tip 43 of catheter 40 may be drawn within bore 34. Within bore 34, near the center of central flange 36, a stop is formed by the shoulder separating the bores 34 and 35, since the diameter of bore 35 is always less than the diameter of bore 34. This stop prevents the removal of connector 31 from the flanged, proximal tip 43 of catheter 40. Accordingly, the practising anesthesiologist can slidably position the two connectors 31 and 51, along with any attendant coupled hoses, without fear that connector 31 will be pulled off the flanged proximal end 43 of connector 40. The anesthesiologist may, if desired, reposition connector 31 to this limit after the surgical operation has been completed and before the intubated catheter or endotracheal tube is to be removed from the patient.

FIG. 5 illustrates the invention as used with cuff-type endotracheal tube 60 having an open distal tip 62, an annular, flanged proximal tip 63, an inflatable cuff 64, and inflation line 65 with attached inflation valve 66. Connector 31 is shown concentrically mounted on the proximal end portion 61 between annular, flanged tip 63 and the point of inserted attachment of inflation line 65.

In this embodiment of the invention, connector 31 is concentrically mounted upon the cylindrical surface of proximal end portion 61 before the affixing of annular flanged tip 63. Connector 31 is, therefore, slidably captured upon endotracheal tube 60, and its limit of axial positioning is confined to the distance between annular, flanged tip 63 and the point of attachment of inflation line 65.

Conventional endotracheal tubes are sized in accordance with the diameters of the lumen of the tubes and may vary from two millimeters to as large as ten millimeters. The outer diameters of such tubes generally vary from three millimeters to approximately twelve millimeters. While the distance between the proximal tip to the point of attachment of the inflation line of cuffed endotracheal tubes varies with the size of the tube, a typical adult size endotracheal tube of seven millimeters internal diameter has a distance of approximately ten to fifteen centimeters between inflation line and proximal tip. It is apparent, therefore, that an appreciable effective shortening of the length of a cuffed endotracheal tube may be achieved by the invention without the necessity of removing a portion of the proximal end by cutting, and without the necessity of removing the connector.

Since many changes may be made in the above-described device and many different embodiments of this invention could be made without departing from the scope thereof, it is intended that all matter contained in the above description or shown in the accompanying drawings shall be interpreted as illustrative and not in a limiting sense.

What is claimed is:

1. A medical appliance comprising in combination:
    (a) a catheter consisting of a hollow, flexible, cylindrical tube having open proximal and distal ends;
    (b) a hollow, cylindrical connector concentrically mounted upon the hollow, flexible, cylindrical tube of said catheter between said open proximal and distal ends, said hollow, cylindrical connector having a hollow, cylindrical input section, a hollow, cylindrical output section, and a central passageway extending therebetween, said hollow, cylindrical input section having a bore of uniform diameter, said hollow, cylindrical output section having a bore of uniform diameter smaller than the diameter of said bore of said hollow, cylindrical input section;
    (c) an annular internal ridge situated within said hollow, cylindrical output section, said annular internal ridge projecting radially inward from the inner cylindrical wall of said hollow, cylindrical output section, said annular internal ridge having a smooth, rounded peripheral tip physically engaging and depressing the outer cylindrical surface of the hollow, flexible cylindrical tube of said catheter; and
    (d) an annular flange attached to the open proximal end of the hollow, flexible cylindrical tube of said catheter, said annular flange having an outer diameter larger than the bore of said hollow, cylindrical output section of said hollow, cylindrical connector and smaller than the bore of said hollow, cylindrical input section of said hollow, cylindrical connector, said hollow, cylindrical connector being axially slidable over the outer cylindrical surface of said hollow, flexible cylindrical tube of said catheter while providing an airtight seal between connector and catheter.

2. The medical appliance as defined by claim 1 wherein said hollow, cylindrical connector further comprises an external central flange situated between said hollow, cylindrical input and output sections, said external central flange serving to grip the hollow, cylindrical connector to facilitate the axial sliding of said connector over the outer cylindrical surface of said catheter.

3. The medical appliance as defined by claim 1 wherein said hollow, cylindrical connector is formed of relatively hard plastic material, and wherein said annular internal ridge situated within said hollow, cylindrical output section is integrally formed as part of said hollow, cylindrical output section.

4. The medical appliance as defined by claim 1 wherein a circular shoulder is formed within the passageway of said hollow, cylindrical connector at the junction of the bores of said hollow, cylindrical input and output sections, said circular shoulder providing a stop to prevent the open proximal end of said hollow, flexible tube, with said attached annular flange, from passing through the passageway of said connector into said hollow, cylindrical output section of said connector.

5. A medical appliance comprising in combination:
    (a) a cuff-type endotracheal tube consisting of a hollow, cylindrical tube of flexible material having open proximal and distal ends, said cuff-type endotracheal tube having an inflatable cuff surrounding the distal end portion of the hollow, cylindrical tube near the open distal end, said cuff-type endotracheal tube having an inflation line attached to the hollow, cylindrical tube between said open proximal and distal ends, said inflation line being adapted for conveying air under pressure to said cuff when said cuff is to be inflated;
    (b) a hollow, cylindrical connector composed of relatively hard material concentrically mounted upon the hollow, cylindrical tube of flexible material forming said endotracheal tube, said hollow, cylindrical connector being positioned on said hollow, cylindrical tube between said inflation line and said open proximal end, said hollow, cylindrical connector having a hollow, cylindrical input section, a hollow, cylindrical output section, a central passageway extending therebetween, and an external central flange situated between said hollow, cylindrical input and output sections, said hollow, cylindrical input section having a bore of first diameter, said hollow, cylindrical output section having a bore of second diameter smaller than said bore of first diameter, an annular internal ridge situated within said hollow, cylindrical output section, said annular internal ridge projecting radially inward from the inner cylindrical wall of said hollow, cylindrical output section, said annular internal ridge having a smooth, rounded peripheral tip physically engaging and depressing the outer cylindrical surface of the hollow, cylindrical flexible tube of said endotracheal tube to form an airtight seal between connector and endotracheal tube; and (c) an annular flange attached to the open proximal end of said hollow, cylindrical tube forming said endotracheal tube, said annular flange having an outer diameter larger than said second diameter of said bore of said hollow, output section and smaller than said first diameter of said bore of said hollow input section, said hollow, cylindrical connector being axially slidable over the outer surface of said hollow, cylindrical tube of flexible material forming said endotracheal tube between said annular flanged proximal end of said endotracheal tube and said inflation line without loss of the airtight seal between said connector and said endotracheal tube.

* * * * *